(12) United States Patent
Yu et al.

(10) Patent No.: US 6,237,392 B1
(45) Date of Patent: May 29, 2001

(54) INSPECTION APPARATUS FOR GAS DETECTORS

(75) Inventors: Gu-Sheng Yu, Taipei; Yao Min Lin, Hsinchu, both of (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/219,014

(22) Filed: Dec. 23, 1998

(30) Foreign Application Priority Data

Jun. 29, 1998 (TW) ................................................ 87210417

(51) Int. Cl.[7] ............................. G01N 1/22; G01N 30/02; G01N 7/00
(52) U.S. Cl. ........................ 73/1.06; 73/19.02; 73/19.05; 73/23.23
(58) Field of Search ................................. 73/19.01, 19.04, 73/23.24, 23.36, 19.02, 19.05, 19.12

(56) References Cited

U.S. PATENT DOCUMENTS 5,528,923 * 6/1996 Ledez et al. ........................ 73/19.12
5,663,488 * 9/1997 Wang et al. ........................ 73/23.25

* cited by examiner

*Primary Examiner*—Hezron Williams
*Assistant Examiner*—Katina Wilson
(74) *Attorney, Agent, or Firm*—Kenyon & Kenyon

(57) ABSTRACT

An inspection apparatus for gas detectors is disclosed which comprises an open-feasibly air-tight testing reservoir in which gas detectors to be tested can be positioned, an air-tight dispensing reservoir for mixing the gas to be tested, a vacuum device for making the testing reservoir and the dispensing reservoir in vacuum, a gas supply device for supplying at least a standard gas and a diluting gas to the dispensing reservoir, and a controlling means for controlling the dispensation of the gases to each of the above-described components of the invention. By means of the invention, the executions of the mixing of the gases and the detection of the gas detector are substantially simultaneous and thus the time consumption as well as the amount of required gas are reduced. Moreover, an automatic control is available when the inspection apparatus of the invention is equipped with a computer.

5 Claims, 2 Drawing Sheets

INSPECTION APPARATUS FOR GAS DETECTORS

BACKGROUND OF THE INVENTION

1. Field of the Invention

The present invention relates to an inspection apparatus for gas detection, particularly to an inspection apparatus which can repeatedly supply a target gas in different concentration to gas detectors for testing the performance and accuracy of the gas detectors during a shorter period and can reduce the amount of gas required.

2. Related Prior art

The known system for examining the accuracy or performance of a gas detector is performed in an open environment. In such a method, a standard gas is first mixed with a diluting gas in a blending reservoir at a proper proportion and then is continuously sent through a gas detector to be inspected so as to serve as a testing gas to the gas detector.

In such an inspection apparatus, the environment around the gas detector is an open one and thus is unstable and uncontrollable due to its ease change with the changes of the atmosphere, such as pressure or the like. Moreover, while changes the concentration of the standard gas to inspect the action of the gas detector under different gas concentration, the gas required to reach the equilibrium of that concentration is approximately ten times more than the volume of the blending reservoir. Including the amount of the gas required to perform the test within a period of time, the total amount of gas consumption will be approximately twenty times more than the volume of reservoir. Thus, it is not only a waste of standard gas and diluting gas, but also a waste of time. Furthermore, releasing the tested gas to atmosphere could create an air pollution problem. It is specially harmful in the case that such a testing gas is toxic.

SUMMARY OF THE INVENTION

Accordingly, one of the objects of this invention is to provide an inspection apparatus for the gas detector which can save both the gas required and the time spent, and achieve the goal for environment protection.

The other object of this invention is to provide an inspection apparatus for the gas detector which can ensure the accuracy of the gas detector.

It is a yet another object of this invention to provide an inspection apparatus for the gas detector which can be automatically controlled to obtain the effectiveness mentioned above.

To achieve the objects mentioned above, the inspection apparatus for gas detectors in accordance with this invention comprises an open-feasibly air-tight testing reservoir, in which a gas detector to be tested can be positioned; an air-tight dispensing reservoir for mixing and preparing the gas to be tested; a vacuum device for making the testing and the dispensing reservoirs reach the vacuum situation; a gas supply means for supplying at least a standard gas and a diluting gas to the dispensing reservoir; and a controlling means for controlling the dispensation of said gases to said reservoirs and transfer of said gases between said reservoirs such that the execution of mixing the gases and the detection of the gas detectors are substantially simultaneous.

For another object mentioned above, the inspection apparatus for gas detectors according to this invention further comprises a standard gas detector for monitoring, simultaneously with the gas detectors to be tested, the gas existing in the testing reservoir so as to double check the accuracy of the gas detectors to be tested.

For yet another object mentioned above, the inspection apparatus for the gas detector according to this invention is characterized in that the control means can be connected to a computer so that the operations of the valves, the vacuum device and the gas supply means, as well as the data acquisition can be automatically controlled under the whole inspection procedure.

According to one aspect of this invention, since the test of the gas detectors is under a sealed space, the testing gas required can be minimized and the environment for testing can remain stable.

According to another aspect of this invention, since the testing gas can be retrieved by means of the vacuum device and thus the air pollution can be prevented especially in the case that the testing gas is toxic.

According to yet another aspect of this invention, due to a provision of the two gas reservoirs, the dispensing reservoir could be used to prepare the standard testing gas at a new concentration when the testing reservoir is provided to perform the testing of the gas detectors and thus the time for inspecting the gas detectors is minimized.

According to a further aspect of this invention, by using a computer to control each of the electrically-actuated valves respectively allocated between each reservoirs and devices, an automatic operation for inspecting the gas detectors is available.

DETAILED DESCRIPTION OF PREFERRED EMBODIMENTS

Figure 1:
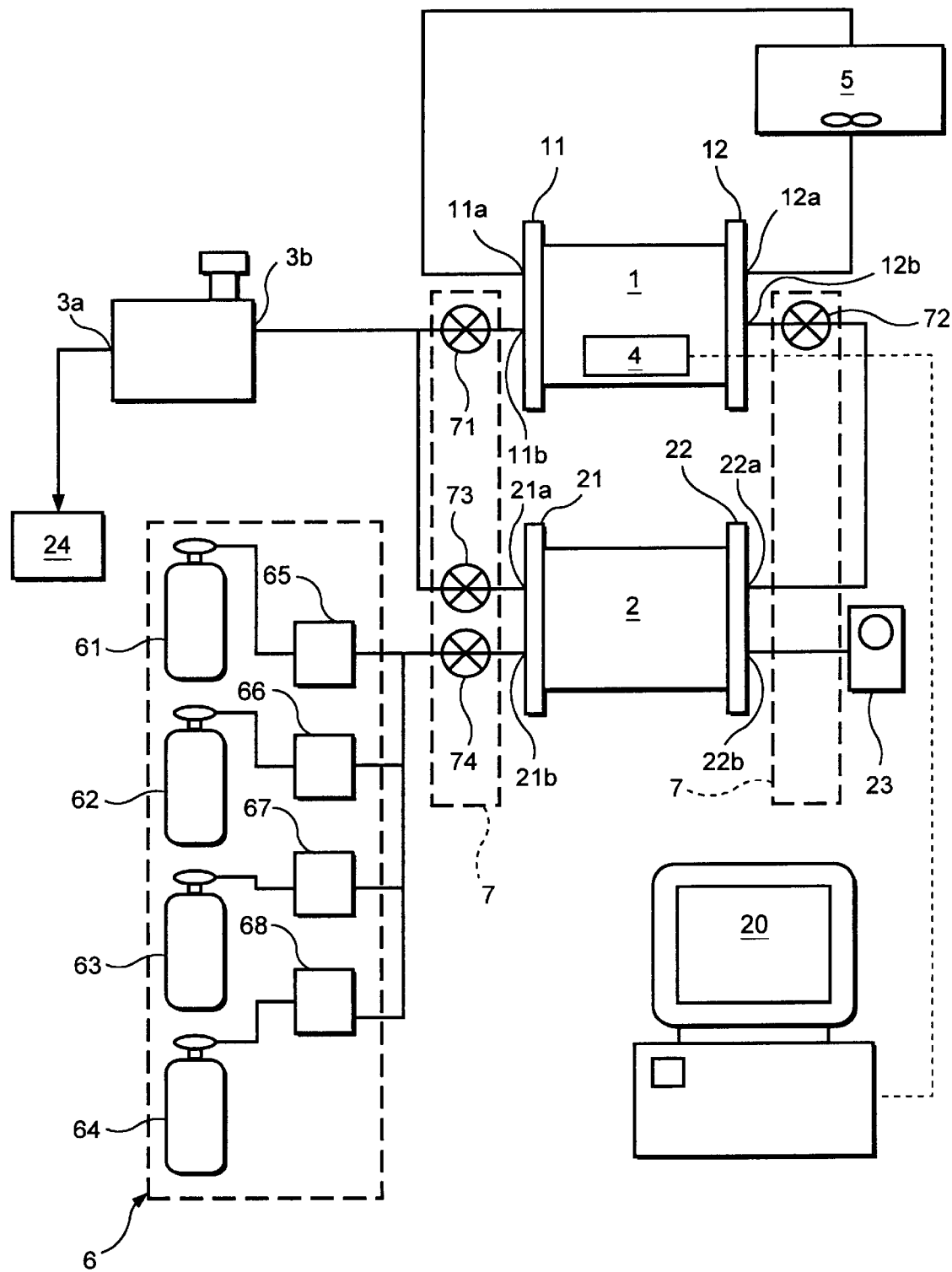
FIG. 1 is a schematic drawing of an inspection apparatus for gas detectors in accordance with the preferred embodiment of this invention.

FIG. 1 illustrates a schematic drawing of an inspection apparatus for gas detectors in accordance with a preferred embodiment of this invention. As shown in FIG. 1, an inspection apparatus for gas detectors in accordance with this invention comprises an open-feasibly air-tight testing reservoir 1, an air-tight dispensing reservoir 2, a vacuum device 3, a gas supply device 6, and a controlling means 7.

The air-tight testing reservoir 1 is a cylinder reservoir with two open ends which are covered with two removable plates 11 and 12 respectively so that gas detectors 4 to be tested can be positioned in the reservoir 1. Each plate 11,12 is air-tightly secured onto the end of the reservoir 1 by using a parking made of such as Teflon, and each plate 11,12 is provided with connecting holes for connecting the interior of the reservoir 1 with other components mentioned below. As shown in FIG. 1, a set of connecting holes 11a, 12a are connected to a standard gas analysis instrument 5, such as an optical type of gas detector, so that the gas analysis instrument 5 is under an environment which is the same as that for the gas detectors 4 and therefore makes a double check to the accuracy of the gas detectors 4. Moreover, an other connecting hole 11b in the plate 11 is connected to an inlet 3b of the vacuum device 3 via a valve 71 while the other hole 12b in the plate 12 is connected to the dispensing reservoir 2 via a valve 72.

The air-tight dispensing reservoir 2 has a structure which is similar to that of the air-tight testing reservoir 1. As shown in FIG. 1, a connecting hole 21a in the plate 21 is connected to an inlet 3b of the vacuum device 3 via a valve 73 and the other hole 21b in the plate 21 is connected to the gas supply device 6 via a valve 74. A connecting hole 22a in the plate 22 is connected to the testing reservoir 1 via the valve 72 while the other hole 22b in the plate 22 is connected to a pressure gauge 23 so as to monitor the pressure in the dispensing reservoir 2.

The gas supply device 6 comprises four gas bottles 61,62,63,64 each filled with different type of gas, and four flow control valves 65,66,67,68, said four mass flow control valves connecting to the outlet of each bottle for controlling the flow output from each bottle. The outputs of the four flow control valves 65,66,67,68 are combined and then input to the dispensing reservoir 2 via the valve 74. Moreover, the bottle 61 is filled with a type of standard full-scale gas that the gas detectors 4 will detect. The bottle 62 is filled with a type of diluting gas for diluting the standard gas. The bottles 63, 64 can be filled with different types of interference gases for testing the influence of the interference gases to the response of the gas detectors.

The vacuum device 3 can be a high vacuum dry pump connecting to the testing reservoir 1 and the dispensing reservoir 2. Its outlet 3a can be connected to a waste gas collecting system to prevent the above gases from releasing to atmosphere.

The valves 71,72,73,74 constitute the control means 7 and each thereof can be a manual valve or an electrically actuated valve.

In case that all the valves 71–74 are electrically actuated valves, all of the valves and the device mentioned above, such as the vacuum device 3 or gas supply device 6, can be electrically controlled by a computer 20 and thus the automatic control is available.

As to the control flow relating to the above embodiment of this invention, it is described as below.

Figure 2:
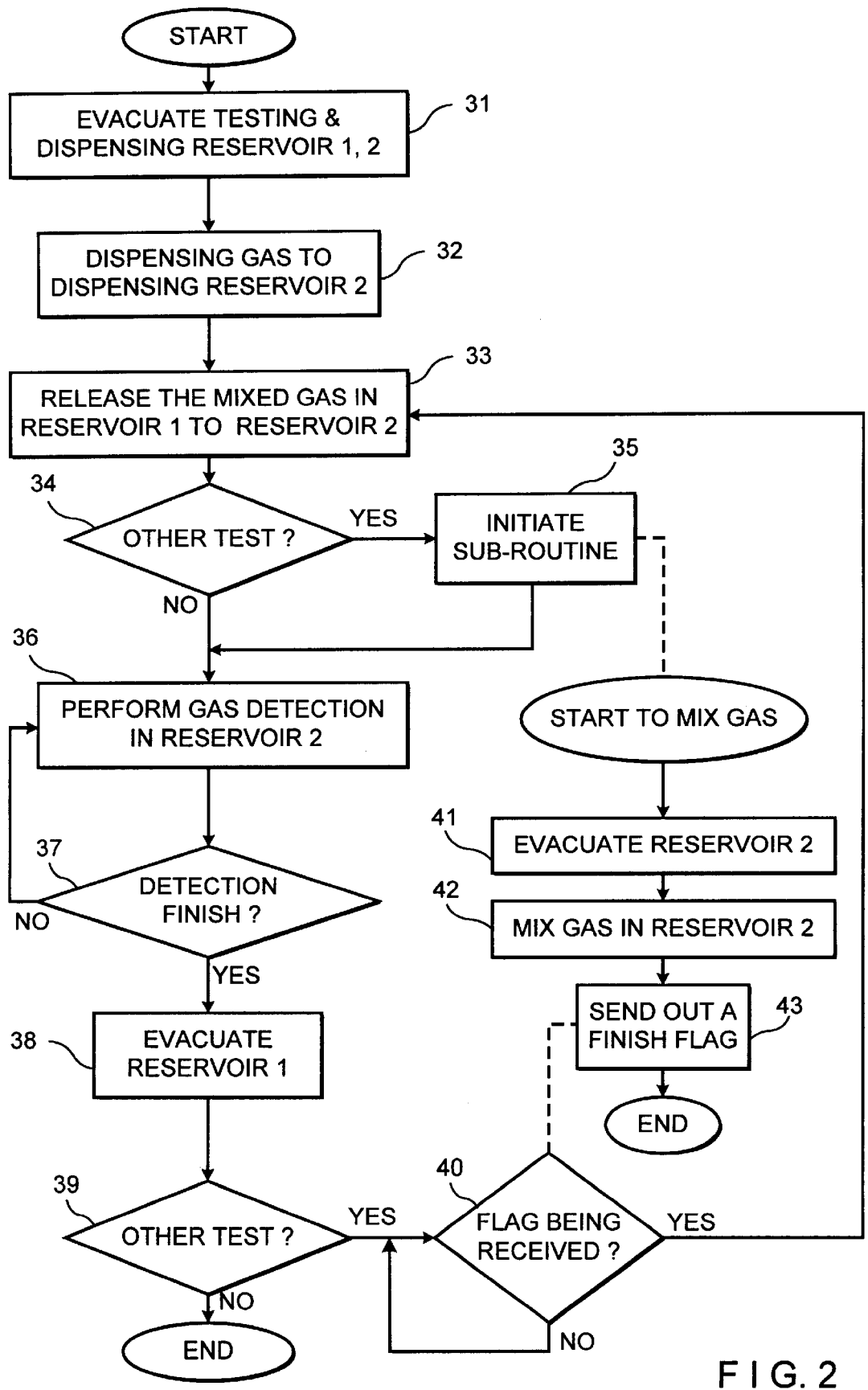
FIG. 2 is a flow chart for the control procedure of the inspection apparatus for gas detector of FIG. 1.

FIG. 2 sets forth a flow chart for controlling the operation of the inspection apparatus in accordance with this invention under a control of the computer 20. First, each of the control valves 71–74 and 65–68 are closed and the gas detectors 4 have been positioned in the testing reservoir 1. Referring to FIG. 2, operation process starts from block 31 by opening the valves 71 and 73, and then turn on the dry pump to evacuate the testing reservoir 1 and the dispensing reservoir 2. When these two reservoirs 1 and 2 reach to a desired vacuum, the valves 71 and 73 are closed and then the process goes into block 32.

Block 32 performs the gas dispensing procedure. In this procedure, valve 74 is opened firstly and then the valve 65 is opened so that the standard gas 61 is applied to the dispensing reservoir 2 until a determined amount of gas is obtained. Thereafter, valve 65 is closed and valve 66 is opened so that the diluting gas 62 is applied to the dispensing reservoir 2 to mix with the standard gas 61. The same to the foregoing procedure, interference gases 63 and 64 are continuously applied to the dispensing reservoir 2 by controlling its corresponding valve, if necessary. Thus, a mixed gas is obtained in the reservoir 2 and then the valve 74 is closed, so the process goes into block 33.

In block 33, the valves 72 is opened for the mixed gas in the dispensing reservoir 2 flows into the testing reservoir 1 via the valve 72 due to the pressure difference between the reservoir 1 and reservoir 2. After the pressure of reservoir 1 and reservoir 2 reaches balance, the pressure will substantially become a half of the original pressure in the dispensing reservoir 2, which can be read out from the pressure gauge 23. In addition, the mixed gas for testing will also flow into the standard gas analysis instrument 5 from the testing reservoir 1. Thereafter, the valve 72 is closed again.

At this time point, it is necessary to determine whether the dispensing reservoir 2 will be used to prepare another concentration of standard gas. If yes, a procedure of filling another type or concentration of gas will be performed in the dispensing reservoir 2 while the gas detection is performing in the testing reservoir 1 simultaneously. Otherwise, after finishing the gas detection, the procedure will go to block 34.

As described above, block 34 decides if another concentration of the standard gas will be tested. If yes, the computer will initiate a sub-routine in block 35 for dispensing gases into the reservoir 2 from the gas supply device 6, if no, the process directly goes into block 36.

In terms of the sub-routine, the steps performed in block 41 are similar to those performed in block 31 except that the testing reservoir 1 will not be evacuated. The steps performed in block 42 are the same as those performed in block 32. When the dispensation of the gases from the gas supply device 6 to the dispensing reservoir 2 is finished in block 32, a finish flag will be sent out in block 43 by the sub-routine.

In block 36, gas detection in testing reservoir 1 is performed. Block 37 is to determine whether or not the detection is finished. The decision is made based on whether the computer 20 receives a stable reading signal or an instruction informing that required reading values are obtained. The gas detection process will go on until the finish message is obtained, and the process will continue to block 36 for evacuating the testing reservoir 1.

After the performance of gas detection is finished in the testing reservoir 1, the valve 71 will be opened and the vacuum device 3 will start to evacuate the testing reservoir 1 until a vacuum is reached as defined in block 38. When the testing reservoir 1 comes to a vacuum, the valve 71 is then closed. At this point, a decision has to be made in block 39 if another test is required. If yes, the testing procedure will go back to block 33 in case that the finish flag coming from the sub-routine is received, as defined in block 40. If no, the process will go to the end and the testing will be finished. In block 40, if the finish flag is not received yet, the procedure going to block 33 will be suspended until it is received. Once the procedure goes back to block 33, the whole testing process after block 33, as described above, will be repeated.

In another aspect, the computer can also be used to monitor or record the data detected by the gas detectors 4 and the standard gas analysis instrument 5 for further processing, such as data analysis and store.

As described above, by means of the provision of two reservoirs and the control device, when the testing reservoir 1 is used for gas detection, the dispensing reservoir 2 can be simultaneously used for preparing a new gas standard at a new concentration. Therefore, the above mentioned embodiment according to the invention is very time-saving, especially for a test that occurs with repetitive procedures. Moreover, the required gas is minimized dramatically due to the closed environment undergoing the gas detection. Furthermore, when the inspection apparatus is combined with a computer, an automatic control is available.

However, the foregoing description of the preferred embodiment of the invention is presented for the purpose of illustration and description. It is not intended to be exhaustive or to limit the invention to the precise form disclosed. Many modifications and variations are possible in light of the above teaching. Therefore, it is intended that the scope of the invention should not be limited to this detailed description, but to the claims appended hereto.

What is claimed is:

1. An inspection apparatus for gas detectors, comprising:
   an open-feasibly air-tight testing reservoir in which gas detectors to be tested can be positioned;
   an air-tight dispensing reservoir for the preparing of the standard gas to be tested;
   a vacuum device for making the testing reservoir and the dispensing reservoir in a vacuum situation;
   a gas supply device for supplying at least a standard gas and a diluting gas to the dispensing reservoir; and
   a controlling means for controlling the dispensation of said gases to said reservoirs and the exhausting of said gases from said reservoirs such that the execution of the mixing and preparing of the gases and the inspection of the gas detectors are substantially simultaneous.

2. The inspection apparatus for the gas detectors as claimed in claim 1, further comprising a standard gas analyzer for monitoring the gas existing in the testing reservoir so as to check the accuracy of the gas detectors to be tested.

3. The inspection apparatus for the gas detectors as claimed in claim 1, wherein the gas supply device further comprises flow control valves for controlling the amount of the gases supplied to the dispensing reservoir.

4. The inspection apparatus for the gas detectors as claimed in claim 1, wherein the control means comprises a first control valve allocated between the testing reservoir and the vacuum device, a second control valve allocated between the vacuum device and the dispensing reservoir, a third control valve allocated between the dispensing reservoir and the gas supply means, and a fourth control valve allocated between the testing reservoir and the dispensing reservoir.

5. The inspection apparatus for the gas detectors as claimed in claim 4, wherein the control means is further combined with a computer so as to electrically control all of the valves, to operate the vacuum device and the gas supply device, to acquire testing data and to automatically control the whole inspection procedure.

* * * * *